US010588861B2

(12) United States Patent
Letourneur et al.

(10) Patent No.: US 10,588,861 B2
(45) Date of Patent: Mar. 17, 2020

(54) CROSSLINKED POLYSACCHARIDE BEADS AND THEIR BIOMEDICAL USES

(71) Applicants: INSERM (Institut National de la Sante et de la Recherche Medicale), Paris (FR); Universite Paris Diderot—Paris 7, Paris (FR)

(72) Inventors: Didier Letourneur, Paris (FR); Catherine Le Visage, Paris (FR); Sidi Mohammed Derkaoui, Paris (FR)

(73) Assignees: Institut National de la Santé et de la Recherche Médicale (INSERM), Paris (FR); Université Paris Diderot—Paris 7, Paris (FR)

( * ) Notice: Subject to any disclaimer, the term of this patent is extended or adjusted under 35 U.S.C. 154(b) by 0 days.

(21) Appl. No.: 16/197,409

(22) Filed: Nov. 21, 2018

(65) Prior Publication Data

US 2019/0083400 A1     Mar. 21, 2019

Related U.S. Application Data

(60) Continuation of application No. 15/172,554, filed on Jun. 3, 2016, which is a division of application No. 13/819,437, filed as application No. PCT/EP2011/064927 on Aug. 30, 2011, now Pat. No. 9,381,250.

(30) Foreign Application Priority Data

Aug. 31, 2010  (EP) ..................................... 10305931

(51) Int. Cl.
| | |
|---|---|
| A61K 9/16 | (2006.01) |
| A61K 9/00 | (2006.01) |
| A61L 27/20 | (2006.01) |
| C08B 37/00 | (2006.01) |
| C08B 37/02 | (2006.01) |
| A61K 47/26 | (2006.01) |
| A61K 9/107 | (2006.01) |

(52) U.S. Cl.
CPC .......... *A61K 9/1652* (2013.01); *A61K 9/0019* (2013.01); *A61K 9/1075* (2013.01); *A61K 9/1682* (2013.01); *A61K 47/26* (2013.01); *A61L 27/20* (2013.01); *C08B 37/0018* (2013.01); *C08B 37/0021* (2013.01); *A61K 9/0024* (2013.01); *A61L 2430/02* (2013.01); *A61L 2430/06* (2013.01); *A61L 2430/20* (2013.01); *Y10T 428/2982* (2015.01)

(58) Field of Classification Search
CPC .. A61K 9/1652; A61K 9/0019; A61K 9/1075; A61K 9/1682; A61K 47/26; A61L 27/20; C08B 37/0018; C08B 37/0021
See application file for complete search history.

(56) References Cited

U.S. PATENT DOCUMENTS 4,152,170 A * 5/1979  Nagase ............... C08B 37/0018
                                                    106/162.7
6,201,039 B1 * 3/2001 Brown ...................... A61F 2/28
                                                    424/423

FOREIGN PATENT DOCUMENTS

WO   WO 2009/047347    *   4/2009

OTHER PUBLICATIONS

Fisher Scientific, Solvent Miscibility Chart, copyright 2018. (Year: 2018).*

* cited by examiner

*Primary Examiner* — Johann R Richter
*Assistant Examiner* — Genevieve S Alley
(74) *Attorney, Agent, or Firm* — W & C IP (57) ABSTRACT

The present inventions relates to beads as biocompatible material adapted for use within the human or animal body. Said beads are highly useful for tissue engineering, in situ tissue regeneration, as well as for drug and/or cells delivery. In addition, said beads may support biotechnological applications such as cell carriers.

10 Claims, 4 Drawing Sheets

CROSSLINKED POLYSACCHARIDE BEADS AND THEIR BIOMEDICAL USES

CROSS-REFERENCE TO RELATED APPLICATIONS

This application is a continuation application of U.S. Ser. No. 15/172,554 filed Jun. 3, 2016, which itself was a divisional application of U.S. Ser. No. 13/819,437 filed Mar. 20, 2013, now U.S. Pat. No. 9,381,250, which was a Rule 371 national stage filing from PCT/EP2011/064927 Aug. 30, 2011, and that international application claimed priority to European Patent Application 10305931.7 filed Aug. 30, 2010.

FIELD OF THE INVENTION

The present invention relates to a method for preparing polysaccharide beads. The present invention further provides beads and their uses in various biomedical fields.

BACKGROUND OF THE INVENTION

Biocompatible materials have received a great interest for different biomedical applications. The attributes of the ideal biocompatible material would include the ability to support cell growth either in vitro or in vivo, the ability to support the growth of a wide variety of cell types or lineages, the ability to be endowed with varying degrees of flexibility or rigidity required, the ability to have varying degrees of biodegradability, the ability to be introduced into the intended site in vivo without provoking adverse events, and the ability to serve as a vehicle or reservoir for delivery of cells, drugs or bioactive substances to the desired site of action.

For this purpose, polysaccharides were shown to be the materials of choice due to their validated biological properties. Indeed, many studies are currently drawn to materials obtained by ionotropic gelation (ability of polysaccharides such as pectin, alginate, carrageenan and gellan to form a gel in the presence of multivalent ions). However, those techniques are limited since they are carried out with a little range of polysaccharide type. In addition, those gels are not suitable for an easy and efficient administration within a human or animal tissue, independently of the size and localization of the target tissue. Lee C S et al. have illustrated the use of calcium-alginate beads also for tissue engineering of bone (Lee C S et al. *Regulating in vivo calcification of alginate microbeads*, Biomaterials 2010, June; 31(18):4926-34). Others have prepared polysaccharide beads from chitosan based polyelectrolytes for drug delivery systems. Further, chitosan based polyelectrolyte complexes were proposed as potential carrier materials in drug delivery systems (Hamman J H et al., *Chitosan based polyelectrolyte complexes as potential carrier materials in drug delivery systems*, J Biomed Mater Res, 2010).

However, the above mentioned polysaccharide beads are not adapted because of the instability of the divalent cations complexes under physiological conditions, and to the little range of potential polysaccharides to be used. In addition, the biocompatible materials currently used can not be easily administrated within a human or animal tissue, independently of the size and localization of the target tissue.

There is thus still a need for a biocompatible material adapted for an injection within the human or animal body and that can be used for biological and therapeutic purposes. Particularly, there is a need for a biocompatible material which would be easily administrated by injection to the human or animal tissue, independently of the site of action and of the size of the targeted region.

SUMMARY OF THE INVENTION

The inventors filled the foregoing need by providing a crosslinking method on polysaccharides that allows obtaining beads without prior chemical modifications of the polysaccharides, and without the use of organic solvents. Said method is thus easy to carry out since the polysaccharides are not subjected to any modification. Thus, the beads present the advantage of being suitable for therapeutic use, since they are free of any contamination and organic solvent. The resulting beads in suspension are stable in physiological fluids. Said beads are biocompatible and injectable material, useful for tissue engineering, in situ tissue regeneration, as well as for drug and/or bioactive substance delivery. In addition, said bead can support biotechnological applications such as cell carriers in vitro and in vivo.

In a first object, the invention relates to a method for preparing polysaccharide beads comprising the following steps:

a) preparing an alkaline aqueous solution comprising an amount of at least one polysaccharide and an amount of a cross linking agent;

b) dispersing said alkaline aqueous solution into an hydrophobic phase in order to obtain a w/o emulsion; and c) transforming the w/o emulsion into polysaccharide beads by placing said w/o emulsion at a temperature from about 4° C. to about 80° C. for a sufficient time to allow the cross-linking of said amount of polysaccharide;

wherein said polysaccharide is selected from the group consisting of dextran, pullulan, agar, alginic acid, starch hyaluronic acid, inulin, heparin, fucoidan, chitosan and mixtures thereof.

In one embodiment, the alkaline aqueous solution comprises a porogen agent. Thus, the invention provides porous polysaccharide beads.

In another embodiment, the alkaline aqueous solution comprises active components, such as for instance hydroxyapatite or preferably nano-hydroxyapatite.

In a further embodiment, the alkaline aqueous solution comprises a drug or a bioactive substance.

In a second aspect, the invention relates to a polysaccharide bead obtainable by the method of the invention.

In a third aspect, the invention relates to a polysaccharide bead obtainable by the method of the invention for use for in situ tissue regeneration.

In a fourth aspect, the invention relates to a polysaccharide bead comprising hydroxyapatite, preferably nano-hydroxyapatite, obtainable by the method of the invention for use for stimulating mineralized bone tissue formation.

In a fifth aspect, the invention relates to a polysaccharide bead obtainable by the method of the invention for use as a cell microcarrier.

In a sixth aspect, the invention relates to a polysaccharide bead obtainable by the method of the invention for use for drug, bioactive substance and/or cell delivery.

In a seventh aspect, the invention relates to a polysaccharide bead comprising drug obtainable by the method of the invention for use for treating cancer.

DETAILED DESCRIPTION OF THE INVENTION

Definition

As used herein, the term "polysaccharide" refers to a molecule comprising two or more monosaccharide units.

As used herein, the term "alkaline solution" refers to a solution having a pH strictly superior to 7.

As used herein, the term "aqueous solution" refers to a solution in which the solvent is water.

As used herein, the term "porogen agent" refers to any solid agent which has the ability to form pores within, a solid structure.

As used herein, the twit "cross-linking" refers to the linking of one polysaccharide chain to another one with covalent bonds.

As used herein, the term "cross-linking agent" encompasses any agent able to introduce cross-links between the chains of the polysaccharides of the invention.

In the context of the invention, the tell is "bead", "particle", and "sphere" are used in an interchangeable manner and refer to polysaccharide composition of the invention having a substantially spherical or ovoid shape.

As used herein, the term "nanobeads" encompasses bead having a size of at least 1 nm and inferior to 1000 nm, the term "microbeads" encompasses beads having a size of at least 1 μm and inferior to 1000 μm, the term "macrobeads" encompasses beads having a size of at least to 1 mm.

As used herein, the term "biodegradable" refers to materials that degrade in vivo to non-toxic compounds, which can be excreted or further metabolized.

As used herein, the term "freeze-drying" refers to the drying of a deep-frozen material under high vacuum by freezing out the solvent (ie. water) and then evaporating it in the frozen state.

In its broadest meaning, the term "treating", "treatment" and "therapy" refers to reversing, alleviating, inhibiting the progress of, or preventing the disorder or condition to which such term applies, or one or more symptoms of such disorder or condition.

As used herein, the expression "bone tissue" refers to calcified tissues (e.g., calvariae, tibiae, femurs, vertebrae, teeth), bone trabeculae, the bone marrow cavity, the cortical bone, which covers the outer peripheries of the bone trabeculae and the bone marrow cavity, and the like. The expression "hone tissue" also encompasses hone cells that are generally located within a matrix of mineralized collagen; blood vessels that provide nutrition for the bone cells; bone marrow aspirates: joint fluids: bone cells that are derived from bone tissues; and may include fatty bone marrow. Finally, bone tissue includes bone products such as whole bones, sections of whole bone, bone chips, bone powder, bone tissue biopsy, collagen preparations, or mixtures thereof. For the purposes of the present invention, the term "bone tissue" is used to encompass all of the aforementioned bone tissues and products, whether human or animal, unless stated otherwise.

As used herein, the expression "bone-related disorders" includes disorders of bone formation and bone resorption. Preferably, the expression "bone related disorders" refers to diseases associated with insufficiency of bone formation or bone loss. Non-limiting examples of bone related disorders are rickets, osteoporosis osteomalacia, osteopenia, bone cancer, arthritis, rickets, bone fracture, bone defects, osteolytic bone disease, osteomalacia, bone frailty, loss of bone mineral density achondroplasia, cleidocranial dysostosis, Paget's disease, osteogenesis imperfecta, osteopetrosis, sclerotic lesions, pseudoarthrosis, periodontal disease, anti-epileptic drug induced hone loss, weightlessness induced bone loss, postmenopausal bone loss, osteoarthritis, infiltrative disorders of bone, metabolic bone diseases, organ transplant related bone loss, adolescent idiopathic scoliosis, glucocorticoid-induced bone loss, heparin-induced bone loss, bone marrow disorders, malnutrition, calcium deficiency, rheumatoid arthritis, hypogonadism. HIV associated bone loss, tumor-induced bone loss, cancer-related bone loss, hormone ablative bone loss, multiple myeloma, drug-induced bone loss, facial bone loss associated with aging, cranial bone loss associated with aging, jaw bone loss associated with aging, skull bone loss associated with aging, and bone loss associated with space travel. Preferably, the bone related disorders, as used herein, are bone fracture, large bone defects, rickets, osteoporosis, osteogenesis imperfecta, osteomalacia, osteopenia, bone cancer, osteolytic bone disease, bone frailty and/or loss of bone mineral density.

As used herein, the expression "cardiac tissue" refers to the tissues within the heart. This expression encompasses epicardium, myocardium and endocardium.

As used herein, the expression "cardiac-related disorders" refers to pathologies connected with defects of the cardiac tissue. This expression encompasses the presence of a damages or injured tissue within the cardiac tissue and the resorption of the cardiac tissue.

Non-limiting examples of cardiac-related disorders are myocardial infarction, stroke, hypertension, coronary heart disease, congestive heart failure, rheumatic heart disease, congenital cardiovascular defects, myocarditis, or arrhytmia.

As used herein, the term 'hydroxyapatite', or "HA" refers to a naturally occurring mineral form of calcium apatite with the formula $Ca_5(PO_4)_3(OH)$, but is usually written $Ca_{10}(PO_4)_6(OH)_2$ to denote that the crystal unit cell comprises two entities. The $OH^-$ ion can be replaced by fluoride, chloride or carbonate, producing fluorapatite or chlorapatite. Preferably, for the purpose of the invention, the $OH^-$ is not replaced. Hydroxyapatite is the major component of bone and teeth matrix and gives bones and teeth their rigidity.

As used herein, the term "nanocristalline hydroxyapatite", or "nano-hydroxyapatite", or "n-HA", refers to hydroxyapatite crystal particles having a size comprised between 10 and 100 nm, preferably between 30 and 60 nm, and most preferably about 50 nm. n-HA suitable for carrying out the present invention is obtained for example by precipitation of a solution of phosphoric acid with a solution of calcium hydroxide.

As used herein, the terms "non-aqueous phase", "lipophilic phase", "hydrophobic phase", and "oily phase" may be used in an interchangeable manner.

As used herein, "w/o emulsion" or 'water-in-oil emulsion", refers to the dispersion of an aqueous phase into a lipophilic phase. The term "w/o emulsion" encompasses stable and non-stable emulsion. In a preferred embodiment, the w/o emulsion is obtained in the absence of a substantial amount of any surfactant. In a most preferred embodiment, the w/o emulsion is obtained in the absence of any surfactant.

As used herein, "surfactant" or "emulsifier" refers to a compound that lowers the surface tension of a liquid, the interfacial tension between two liquids, or that between a liquid and a solid.

As used herein, the expression, "in the absence of a substantial amount of surfactant" refers to the absence of surfactant or the presence of a quantity of surfactant which does not interfere with the process of obtaining a w/o emulsion. Therefore, said expression encompasses the possibility of the presence of surfactant in a quantity that would not play its role of lowering the surface tension, therefore not interfering in the properties or size of the polysaccharide beads obtained by the method of the invention. As used herein, "in situ tissue regeneration" refers to the regeneration of a damaged or injured tissue, possibly leading to the restoration of the function of said tissue. This term encompasses all the strategies of providing means, such as the polysaccharide beads of the invention, for promoting the regeneration of a tissue, especially a defective tissue.

Crosslinked Polysaccharide Beads and Method for Preparing Thereof

In a first object, the invention relates to a method for preparing polysaccharide beads comprising the following steps:
 a) preparing an alkaline aqueous solution comprising an amount of at least one polysaccharide and an amount of a cross linking agent;
 b) dispersing said alkaline aqueous solution into an hydrophobic phase in order o obtain w/o emulsion; and
 c) transforming the w/o emulsion into heads by placing said w/o emulsion at a temperature from about 4° C. to about 80° C. for a sufficient time to allow the cross-linking of said amount of polysaccharide,
wherein said polysaccharide is selected from the group consisting of dextran, pullulan, agar, alginic acid, hyaluronic acid, inulin, heparin, fucoidan, chitosan and mixtures thereof.

Typically, the step b) of dispersing the alkaline aqueous solution into the hydrophobic phase is performed under mechanical stirring. Typically, such a dispersing step is performed during 10 min. Alternatively, the emulsification process can be performed using a high performance disperser, such as Polytron® Homogenizer.

In a preferred embodiment, step b) is performed in the absence of a substantial amount any surfactant. In a most preferred embodiment, step b) is performed in the absence of any surfactant. The polysaccharide beads obtained thereof have a mean diameter of more than about 10 µm.

In a specific embodiment, the method of the invention further comprises the following steps:
 d) submerging said polysaccharide beads into an aqueous solution; and
 e) washing said polysaccharide beads.

Typically, the polysaccharide beads are washed in water or phosphate buffer saline (PBS).

In another embodiment, the method of the invention further comprises a step f) of calibrating the polysaccharide beads according to their size. After performing said step of calibrating, the person skilled in the art may obtain beads of a size comprised between about 10 µm to about 5000 µm. Typically, the polysaccharide beads are calibrated according to their size using appropriate nylon filter. The person skilled in the art is aware of the nylon filter adapted for the purpose of the invention.

In still another embodiment, the method of the invention further comprises a step g) of freeze-drying said polysaccharide beads. Freeze-drying may be performed with any apparatus known in the art. There are essentially three categories of freeze dryers: rotary evaporators, manifold freeze dryers, and tray freeze dryers. Such apparatus are well known in the art and are commercially available such as a freeze-dryer Lyovac (GT2, STERIS Rotary vane pump, BOC EDWARDS). Basically, the vacuum of the chamber is from 0.1 mBar to about 6.5 mBar. The freeze-drying is performed for a sufficient time to remove at least 98.5% of the water, preferably at least 99% of the water, more preferably at least 99.5%. Typically, the freeze drying step is performed for 24 hours.

Preferably, the polysaccharide is a mixture of pullulan/dextran. Typically, the weight ratio of pullulan to dextran is 75:25 w/w.

Typically, said cross-linking agent is selected from the group consisting of trisodium trimetaphosphate (STMP), phosphorus oxychloride ($POCl_3$), epichlorohydrin, formaldehydes, carbodiimides, and glutaraldehydes. Preferably, for the purpose of the present invention, said cross-linking agent is STMP.

Typically, the weight ratio of the polysaccharide to the cross linking agent is in the range from 15:1 to 1:1, preferably 6:1.

The skilled artisan is aware of the hydrophobic phases suitable for the purpose of the present invention. Non-limiting examples of hydrophobic phases are vegetal oils, such as canola oil, corn oil, cottonseed oil, safflower oil, soybean oil, extra virgin olive oil, sunflower oil, palm oil, MCT oil, and trioleic oil. Preferably, for the purpose of the present invention, said hydrophobic phase is canola oil. Alternatively, said hydrophobic phase is a silicon fluid. Typically, the quantity of hydrophobic phase in the w/o emulsion (volume of lipophilc phase/volume of the water-in-oil emulsion; v/v) represents from about 10% to about 90% v/v, preferably from about 20% to about 80% v/v, preferably from about 50% to about 80% v/v and most preferably about 70% v/v of the w/o emulsion.

In one embodiment of the invention, the alkaline aqueous solution further comprises an amount of a porogen agent. Thus, the invention also provides porous polysaccharide beads. Non-limiting examples of porogen agents are sodium chloride, calcium chloride, ammonium carbonate, ammonium bicarbonate, calcium carbonate, sodium carbonate, and sodium bicarbonate and mixtures thereof. Preferably, for the purpose of the invention, said porogen agent is sodium chloride. Typically, the weight ratio of the polysaccharide to the porogen agent is in the range from 50:1 to 1:50. In a preferred embodiment, such weight ratio of the polysaccharide to the porogen agent is about 12:14.

Typically, the density of the pores is from about 4% to about 75%, preferably from about 4% to about 50%. The person skilled in the art may easily adapt the porosity of the beads obtained by the method of the invention by adapting the amount of porogen agents added in the alkaline solution.

Typically, the size of the pores of the polysaccharide beads of the invention is comprised between about 1 µm and about 1000 µm. The presence of said pores are highly convenient for incorporating drugs or cells on the surface of the polysaccharides heads of the invention.

In still another embodiment, the alkaline aqueous solution further comprises hydroxyapatite, preferably nano-hydroxyapatite. The invention thus provides polysaccharide beads comprising n-HA. Said polysaccharide beads are founds to be highly appropriate for use for treating of bone disorders.

In the context of the present invention, nano-hydroxyapatite may be a commercial nano-hydroxyapatitc, such as those commercialised by Inframat Corporation or Fluidinova. Preferably, nanocristalline hydroxyapatite useful in the context of the present invention is obtained through chemical precipitation at room temperature of a solution of phosphoric acid, at a concentration comprised between 0.3 to 1M, preferably 0.6M, with a solution of calcium hydroxide, at a concentration comprised between 0.5 to 1.5M, preferably 1M.

Typically, the concentration of nano-hydroxyapatite in the alkaline aqueous solution (w/v) is comprised between 1 and 10% w/v, preferably between 1 and 5% w/v, more preferably between 1 and 3% w/v.

In a further embodiment, the alkaline solution further comprises a drug. The invention thus provides polysaccharide beads comprising a drug, said polysaccharide beads being highly adapted for administering said drug within a target tissue in the human or animal body. Typically, said drug is a drug having an acknowledged therapeutic effect, such as hormones radioactive substance, fluorescent substance, chemotactic agent, antibiotic, steroidal or non-steroidal analgesic, immunosuppressant, or anti-cancer drug. Preferably, said drug is an anti-cancer drug.

In a further embodiment, the alkaline solution further comprises a bioactive substance. Typically, said bioactive substance is a substance known for playing an important role in various mechanisms such as modification of cellular pathways and modification of cellular or tissular responses. Said bioactive substance is chosen among growth factors, cytokines (lymphokines, interleukins and chemokines), antioxidant molecules, angiogenic molecule, anti-angiogenic agents, immunomodulating agents, proinflammatory cytokines, antiinflammatory cytokines, plasma-derived bioactive substances, PRP (platelet rich plasma)-derived substances, soluble adhesion molecules.

In a further embodiment, the alkaline solution further comprises iron oxide. The invention thus provides polysaccharide beads comprising iron oxide particles, highly adapted for use in cancer treatment based on hyperthermia.

Typically, the iron oxide particles ($Fe_2O_3$) may be obtained by alkaline coprecipitation of iron (III) and iron (II) salts. Typically, the concentration of iron oxide in the alkaline aqueous solution is comprised between 0.005 and 0.5 mol/L, preferably between 0.01 and 0.05 mol/L.

In one embodiment, gelatin is added to the w/o emulsion obtained in step b) of the method of the invention. Preferably, said gelatin is added during step c) of the method of the invention, i.e. during the cross linking step. Typically, the concentration of gelatin in the w/o emulsion solution (w/v) is comprised between 1 and 20% w/v, preferably between 1 and 10% w/v, more preferably between 5 and 10% w/v. Addition of gelatin has been shown to enhance adhesion of anchorage-dependent cells onto the beads during in vitro culture.

In a further embodiment, the polysaccharide of the invention is labelled with a fluorescent dye. As used herein, the term "fluorescent dye" refers to any organic or inorganic molecule that absorbs electromagnetic radiation at a given wavelength and that emits electromagnetic radiation of longer wavelength by a fluorescent mechanism upon irradiation by a source of electromagnetic radiation, such as a lamp, a photodiode, or a laser. The invention thus provides polysaccharide beads having a size of less than 10 µm and comprising a fluorescent agent. Said beads are highly appropriate for monitoring the development of a thrombus. Indeed, the inventors have shown that when injected into a patient likely to be suffering from thrombus, the fluorescent head may allow assessing and thus preventing a thrombus to occur. Fluorescent beads are appropriate for monitoring cell infiltration during in vitro culture.

A non-limitative list of fluorescent dyes appropriate in the context of the invention is Fluorescein isothiocyanate (FITC), Rhodamine, Texas red, fluorescent dyes from the Cy family such as Cy2, Cy3, Cy5, Cy5.5, Cy7, fluorescent dyes from the Alexa family such as Alexa 488, Alexa 532, Alexa 546, Alexa 548 Alexa 568, Alexa 594, Alexa 633, Alexa 647 Alexa 660, and indocyanine green.

Preferably, said polysaccharide is chosen in the group consisting of dextran labeled with FITC, pullulan labeled with Rhodamine and their mixtures.

In one particular embodiment, the method of the invention may comprise a further step consisting of hydrating the polysaccharide beads as prepared according to the invention. Said hydration may be performed by submerging the polysaccharide beads in a solution, preferably an aqueous solution (e.g., de-ionized water, water filtered via reverse osmosis, a saline solution, or an aqueous solution containing a suitable active ingredient) for an amount of time sufficient to produce a polysaccharide bead having the desired water content. Typically, when a polysaccharide bead comprising the maximum water content is desired, the polysaccharide bead is submerged in the aqueous solution for an amount of time sufficient to allow the polysaccharide bead to swell to its maximum size or volume. Typically, the polysaccharide bead is submerged in the aqueous solution for at least about 1 hour, preferably at least about 2 hours, and more preferably about 4 hours to about 24 hours. It is understood that the amount of time necessary to hydrate the polysaccharide bead to the desired level will depend upon several factors, such as the composition of the used polysaccharides, the size (e.g., thickness) of the polysaccharide beads, and the temperature of the solution, as well as other factors.

In a second aspect, the invention relates to polysaccharide beads obtainable by the method of the invention. These polysaccharide beads are indeed the only ones which have the remarkable properties provided by the invention.

Typically, said polysaccharide beads have a size comprised from about 5 nm to about 5 mm, preferably about 10 nm to about 1 mm, preferably from about 1 µm to about 100 µm, preferably from about fpm to about 3 µm.

In one embodiment of the invention, when step h) of the method of the invention is carried out in absence of surfactant, the size of the polysaccharide bead obtained thereof is at least about 10 µm. In another embodiment of the invention, when step b) of the method of the invention is carried out in the presence of surfactant, the size of the polysaccharide bead obtained thereof is less than about 10 µm, and is preferably comprised between about 5 nm and about 10 µm.

The size of the polysaccharide beads would be chosen with precaution by the skilled man in regard with the desired use. The size of the polysaccharide beads of the invention is dependent on the characteristics and parameters of the method of preparing such polysaccharide beads. Typically, the size of the polysaccharide bead of the invention may depend on the nature of the polysaccharide, the agitation provided during the process and the distribution of the polysaccharide within the polysaccharide beads. The person skilled in the art may easily adapt and calibrate the beads in order to obtain a desired size. Typically, said adaptation and/or calibration may be performed by the following techniques: sieving or filtration though nylon filter.

The method of the invention can further include the step of sterilizing the polysaccharide beads using any suitable process. The polysaccharide beads can be sterilized at any suitable point. A suitable irradiative sterilization technique is for example an irradiation with Cesium 137, 35 Gray for 10 minutes. Suitable non-irradiative sterilization techniques include, but are not limited to, UV-exposure, gas plasma or ethylene oxide methods known in the art. For example, the polysaccharide beads can be sterilized using a sterilization system which is available from Abtox, Inc of Mundelein, Ill. under the trade mark PlazLyte, or in accordance with the gas plasma sterilization processes disclosed in U.S. Pat. Nos. 5,413,760 and 5,603,895.

The polysaccharide beads produced by the method of the invention can be packaged in any suitable packaging material. Desirably, the packaging material maintains the sterility of the polysaccharide beads until the packaging material is breached.

The person skilled in the art may provide desired properties to the polysaccharide beads according to the invention. Typically, the person skilled in the art may add a compound chosen in the group consisting of a biomolecule, an antimicrobial agent, a surfactant, a differentiation agent, a growth factor and a fluorescent agent.

The techniques for incorporating said compounds in the polysaccharide bead of the invention completely falls within the ability of the person skilled in the art.

Typically, because of the presence of pores on the surface of the polysaccharide beads according to the invention, said compounds may be incorporated on said head, preferably by sowing. In this particular embodiment, said compound would be on the surface of the polysaccharide beads of the invention. Alternatively, said compounds may be added directly the alkaline solution of step a) of the method of the invention. In this particular embodiment, the compound would be within the structure of the polysaccharide heads of the invention. Alternatively, said compounds can be incorporated into the heads during a step consisting of hydrating the polysaccharide beads with a solution of the compound.

In one embodiment, the polysaccharide beads of the invention further comprise one or more biomolecules. Non-limiting example of biomolecules are drugs, hormones, antibiotics such as gentamicin ou vancomycin, proteases and anti-proteases, chemotactic agents, antibiotics, steroidal or non-steroidal analgesics, immunosuppressants, anti-cancer drugs, short chain peptides, glycoprotein, lipoprotein, cell attachment mediators, biologically active ligands, integrin binding sequence, ligands, small molecules that affect the upregulation of specific growth factors, tenascin-C, hyaluronic acid, chondroitin sulphate, fibronectin, decorin, thromboelastin, thrombin-derived peptides, and mixtures thereof. The use of said biomolecules may enhance treatment effects, indicate proper orientation, resist infection, promote healing, increase softness or any other desirable effect. Thus, the polysaccharide beads of the invention comprising a biomolecule are highly adapted for use for delivering a drug. The inventors have included an active drug used as a thrombolytic agent, called tissue-type plasminogen activator (t-PA).

In another embodiment, the polysaccharide beads of the invention further comprise anti-inflammatory agents. Non-limiting examples of anti-inflammatory agents are indomethacin, salicylic acid acetate, ibuprofen, sulindac, piroxicam, and naproxen; thrombogenic agents, such as thrombin, fibrinogen, homocysteine, and estramustine; and radio-opaque compounds, such as barium sulfate, gold particles and iron oxide nanoparticles (USPIOs) and mixtures thereof. In still another embodiment, the polysaccharide beads of the invention further comprise additives. The amount of the additive used depends on the particular application and may be readily determined by one skilled in the art using routine experimentation.

In still another embodiment, the polysaccharide beads of the invention further comprise an antimicrobial agent. Suitable antimicrobial agents are well known in the art. Non-limiting examples of suitable antimicrobial agents are alkyl parabens, such as methylparaben, ethylparaben, propylparaben, and butylparaben; cresol; chlorocresol; hydroquinone; sodium benzoate; potassium benzoate; triclosan and chlorhexidine and mixture thereof. Other examples of antibacterial agents and of anti-infectious agents that may be used are, in a non-limiting manner, rifampicin, minocycline, chlorhexidine, silver ion agents and silver-based compositions and mixtures thereof.

In still another embodiment, the polysaccharide beads of the invention further comprise at least one surfactant. Surfactant, as used herein, refers to a compound that lowers the surface tension of water. The surfactant may be an ionic surfactant, such as sodium lauryl sulfate, or a neutral surfactant, such as polyoxyethylene ethers, polyoxyethylene esters, and polyoxyethylene sorbitan and mixtures thereof.

In one embodiment, the polysaccharide beads of the invention further comprise a differentiation agent. Preferably, such a differentiation agent is an agent involved in bone formation. Alternatively, such a differentiation agent is an agent involved in osteogenesis, angiogenesis or wound healing. Preferably, said differentiation agent is a growth factor. Non-limiting examples of growth factor suitable for the purpose of the present invention are epidermal growth factor (EGF), insulin-like growth factor (IGF-I, IGF-II), transforming growth factor beta (TGFβ), heparin binding growth factor (HBGF), stromal derived factor (SDF-1); vascular endothelial growth factors (VEGF), fibroblast growth factors (FGFs), platelet derived growth factors (PDGF), parathyroid hormone (PTH), parathyroid hormone related peptide (PTHrP), basic fibroblast growth factor (bFGF); TGFβ superfamily factors; Bone morphogenetic protein (BMP) preferably BMP2, BMP3, BMP4, BMP5, BMP7, somatropin, growth differentiation factor (GDF) and mixtures thereof.

Typically, the growth factor is present at a concentration comprised from 1 ng to 100 μg per gram of polysaccharide bead.

In another embodiment, the polysaccharide beads of the invention further comprise cells, such as yeast cells, mammalian cells, insect cells, and plant cells. Preferably, such cell is a mammalian cell. Non-limiting examples of mammalian cells suitable for the purpose of the invention are differentiated cells such as endothelial cells, smooth muscle cells, fibroblasts, chondrocytes, fibrochondrocytes, osteocytes, osteoblasts, osteoclasts, synoviocytes, epithelial cells and hepatocytes or stem cells, embryonic stem cells, human umbilical vein endothelial cells, induced progenitor stem cells (iPS), mesenchymal stem cells from different sources, bone marrow, adipose tissue, peripheral blood progenitor cells, cord blood progenitor cells, genetically transformed cells and mixtures thereof. Typically, because of the presence of pores on the surface of the polysaccharide beads according to the invention, said cells are incorporated on said beads by well-know techniques such as infiltration through submerging the polysaccharide beads of the invention in an aqueous solution comprising said cells. Typically, a suspension of cells is placed on the lyophilised polysaccharide beads of the invention. The bead comprising said cells are then incubated in order to cultivate said cells.

Use of the Crosslinked Polysaccharide Beads According to the Invention

In a third aspect, the invention relates to a polysaccharide bead obtainable by the method of the invention for use for in situ tissue regeneration. The polysaccharide beads of the invention may indeed be infiltrated by cells and thus promote tissues regeneration. Said polysaccharide bead are thus are indeed highly adapted for injection or deposition within a defective tissue. Preferably, said defective tissue is cardiac tissue, bone or cartilage tissue, or muscle tissue. The polysaccharide beads of the invention are thus highly useful for stimulating heart and muscle regeneration.

In one particular embodiment, said polysaccharide beads may be implanted within the cardiac tissue for treating myocardial infarction. Therefore, the polysaccharide beads of the invention are useful for cardiac repair and development.

In another embodiment, the invention relates to a polysaccharide bead comprising n-HA obtainable by the method of the invention for bone regeneration. The inventors have indeed shown the ability of the porous polysaccharide beads according to the invention to stimulate the production of an extracellular mineralized matrix and probably through differentiation of cells into bone cells. Said polysaccharide beads are thus highly adapted for use in the treatment of bone related disorders. Indeed, they are highly effective since their size can be adapted to the size and localization of the bone to treat or to regenerate.

For the purpose of the invention, the polysaccharide beads of the invention may be administrated within a desired location with the help of any method suitable know by the skilled man. Typically, the polysaccharide beads may be implanted with the help of a needle. The needle would be chosen according to the size of the polysaccharide beads to be administrated. Alternatively, the polysaccharide beads may be implanted with the help of a catheter. Such catheter may be porous or may present needle to improve the administration within the desired location. Macrobeads in bone defects for instance could also be deposited via a spatula or any appropriate grip.

In a fourth aspect, the invention relates to a polysaccharide bead comprising hydroxyapatite, preferably nano-hydroxyapatite, obtainable by the method of the invention for use for stimulating ectopic hone mineralized tissue formation. In the context of the present invention, the expression "ectopic" refers to a non osseous tissue. Therefore, the invention also relates to a polysaccharide bead obtainable according to the method of the invention for use for inducing mineralized tissue in a non-osseous site.

The inventors have shown that administering polysaccharide beads comprising n-HA according to the invention lead to the stimulation of a dense collagen network and blood vessel formation as well as the recruitment of osteoblast-like cells. Such an administration of polysaccharide beads in subcutaneous site leads to the formation of a dense mineralized tissue and thus to bone formation. Preferably, such stimulation of ectopic mineralization occurs in absence of stem cells and in absence of growth factors included in the polysaccharide beads prior to injection. Indeed, the inventors have shown that the polysaccharide beads comprising n-HA according to the invention have the ability to induce mineralized tissue in a non-osseous site and in osseous site. Therefore, the invention provides polysaccharide beads for use for stimulating mineralized tissue formation in osseous site, as well as in non-osseous site, in the presence as well as in the absence of stem cells and/or growth factors.

In a fifth aspect, the invention relates to a polysaccharide bead obtainable by the method according to the invention for use as a cell microcarrier. The polysaccharide beads of the invention have indeed also been found to be highly adapted for use as a cell microcarrier, especially for use in bioreactor. Such strategy may be useful for growing anchorage-dependent cells such as animal cells, on the surface of the microsphere according to the invention. Thus, this strategy allows the growth of anchorage dependent cells in a suspension culture. The use of those polysaccharide beads is thus an attractive alternative to conventional monolayer cell culture method.

In a sixth aspect, the invention relates to a polysaccharide head obtainable by the method according to the invention for use for drug and/or cell delivery. In one embodiment, the polysaccharide beads of the invention may comprise a drug or cells and are able to deliver said drug or cells within a specific tissue. Because of its very nature and composition in polysaccharide, the polysaccharide beads of the invention are highly inclined to degradation within a specific tissue. Such disintegration may lead to the delivery of a drug or cells to the localization of interest. The polysaccharide beads of interest are porous or not according to the application and type of delivery. In another embodiment, the polysaccharide beads of the invention are infiltrated by a drug, a bioactive substance, and/or cells. Said infiltration is performed by submerging the polysaccharide beads of the invention in an aqueous solution comprising said drugs and/or cells. Typically, said solution can be hydrophilic or hydrophobic, depending on the nature of the drug to be infiltrated within the polysaccharide beads. Alternatively, the alkaline solution of step a) of the method of the invention comprises a drug, therefore providing a polysaccharide bead useful for drug delivery.

Typically, the suitable drugs are drugs having an acknowledged therapeutic effect, such as hormones, radioactive substances, fluorescent substances, chemotactic agents, antibiotics, steroidal or non-steroidal analgesics, immunosuppressants, anti-cancer drugs.

Typically the bioactive substance is a chosen among growth factors, cytokines (lymphokines, interleukins, and chemokines), antioxidant molecules, angiogenic molecule, anti-angiogenic agents, immunomodulating agents, proinflammatory cytokines, antiinflammatory cytokines, plasma-derived bioactive substances, PRP (platelet rich plasma)-derived substances, soluble adhesion molecules.

Typically, the polysaccharide beads of the invention loaded with a drug and/or a bioactive substance are administrated within the human or animal body by injection usually subcutaneous, intramuscular or intraosseous. The loaded polysaccharide beads are then able to release the drug and/or bioactive substance in a consistent way over a long period of time.

Preferably, said drug is an anti-cancer drug. Thus, the invention provides polysaccharide bead comprising an anti-cancer drug, highly useful for treating cancer. The polysaccharide beads of the invention loaded with anticancer drugs are appropriate for use for treating solid tumors, for instance, sarcomas, carcinomas, and lymphomas. Treatment of solid tumors varies based on the type, location and stage of tumor. Once at the target site, the drug is released from the polysaccharide beads creating a high local concentration in the tumor tissue.

The polysaccharide beads of the invention may also be used as drug depot implant. Said way of administering a drug is advantageous since it allows a slow release of an effective therapeutic amount of said drug into a desired location over a prolonged period of time. The drug is thus delivered in optimal conditions. Said polysaccharide bead loaded with a drug, used as drug depot implant may be administered according to suitable techniques, known by the skilled person in the art. For example, said polysaccharide beads may be administered by injection by syringe and/or catheter, or forceful injection by gun. Drug depot implant strategy may be performed with various type of drug, such as decanoate salts or esters. Typically, said polysaccharide bead used as a drug depot implant are advantageous for administrating antibiotics and/or anti-cancer drugs within a defective bone. For example, said polysaccharide bead may comprise gentamicin and/or vancomycin and be applied via an intraosseous administration.

In a seventh aspect, the invention relates to a polysaccharide bead comprising iron oxide obtainable by the method according to the invention for use for treating cancer. The polysaccharide beads of the invention comprising iron oxide are adapted for use for local heat generation (hyperthermia) in cancer treatment. When exposed to a high frequency magnetic field, the polysaccharide bead comprising iron oxide generates heat through oscillation. Direct injection of said polysaccharide beads into solid tumors, followed by exposure to an alternating magnetic field, is capable of inducing tumor regression. Polysaccharide beads loaded with both magnetic nanoparticles and anticancer drugs such as doxorubicin or paclitaxel allow to combine hyperthermia and drug delivery strategies for treating cancer.

In an eighth aspect, the invention relates to a polysaccharide bead comprising a fluorescent dye obtainable by the method according to the invention for use for real-time assessment of cardiac perfusion, and acute intravascular thrombi. Preferably, said bead have a size of less than 10 µm. Preferably, the invention relates to a polysaccharide head comprising a fluorescent dye obtainable by the method according to the invention for use for assessing thrombus in a subject likely to develop one. Indeed, the polysaccharides beads of the invention comprising a fluorescent dye are highly appropriate for intravenous injection. Cardiac perfusion can then easily be imaged in real time.

EXAMPLES

Preparation of Macro/Micro Beads

A water-in-oil (w/o) emulsification process was performed to obtain polysaccharide micro/macro beads.

Beads were prepared using a blend of pullulan/dextran 75:25 (pullulan, MW 200,000, Hayashibara Inc; Dextran MW 500,000, Pharmacia), prepared by dissolving 9 g of pullulan and 3 g of dextran into 40 mL of distilled water.

Chemical cross-linking was carried out using trisodium trimetaphosphate STMP (Sigma) under alkaline condition. 100 µL of 10M sodium hydroxide was added to 1 g of the polysaccharide blend, followed by the addition of 100 µL of water containing 30 mg of STMP. This polysaccharide/NaOH/STMP mixture was then dispersed into 100 mL of canola oil under mechanical stirring for 10 min.

The w/o emulsion was then cross-linked at 50° C. for 20 min. Resulting heads were collected by centrifugation (2000 rpm, for 3 min), washed extensively with PBS (10×) then 0.025% NaCl solution, calibrated according to their size using nylon filters and freeze-dried for 24 h until complete removal of water (FIG. 1, top).

Figure 1:
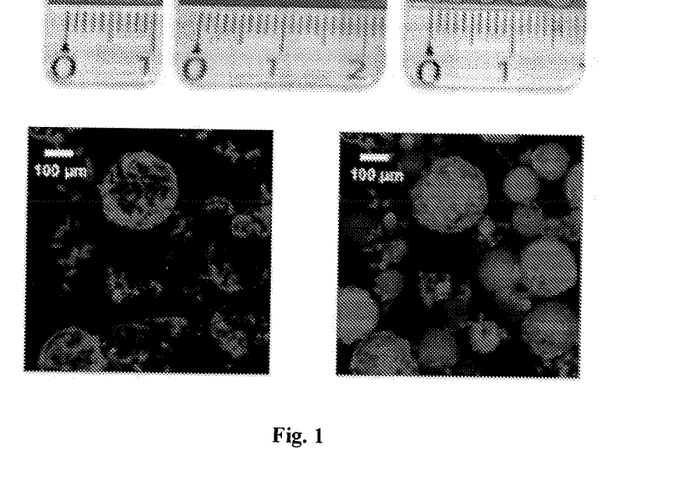
FIG. 1: Macroscopic view of beads as macro/microcarriers. The top panel evidences the beads after crosslinking (left), after freeze-drying (middle), and after hydratation (right). The bottom panel is an example of beads observed on confocal microscopy incubated with vascular cells that attached to the bead surfaces for further use in vitro in a bioreactor, or in vivo for cell delivery. FITC-dextran was used in the composition of the beads and cells were previously labeled with TRITC-phalloidin for identification on the bead surface.

Human endothelial cells cultured with beads can be observed on their surface (FIG. 1, bottom). For confocal analysis, FITC-dextran was used and cells were labeled with TRITC-phalloidin.

In another experiment, (w/o) emulsification process was conducted using a high performance disperser (Polytron® Homogenizer) in order to obtain smaller beads (<50 µm).

Preparation of Porous Macro/Micro Beads

In another experiment, porous microbeads could be prepared. In this process, porogen agent such as NaCl (14 g) was added into the polysaccharide solution before cross-linking.

Figure 2:
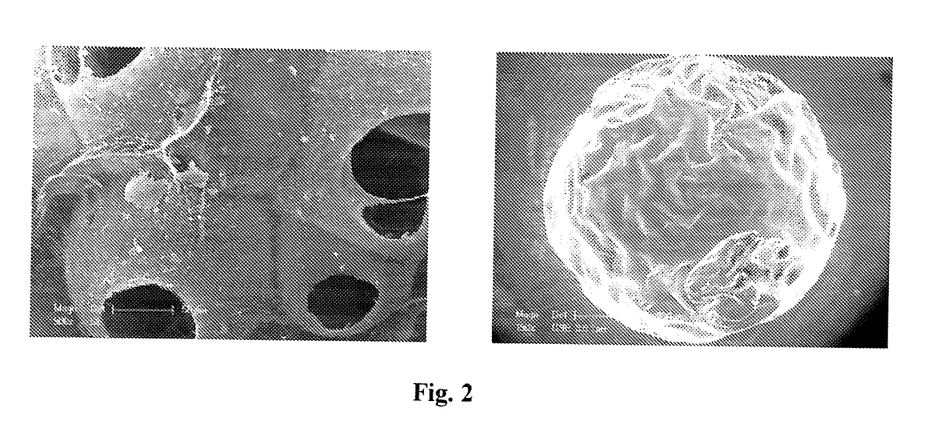
FIG. 2: The morphology of freeze-dried porous heads was analyzed by scanning electron microscopy (left, scale bar: 50 µm). After rehydradation in PBS, hydrated beads were observed with Environmental Scanning Electron Microscopy (ESEM Philips XL 30, Netherlands) (right, scale bar: 200 µm).

The resulting macro/micro beads were further characterized by confocal analysis and electronic microscopies. Beads prepared with NaCl as a porogen agent were porous (FIG. 2). The morphology of freeze-dried porous beads was evidenced by scanning electron microscopy (FIG. 2, left). After rehydradation in PBS, hydrated porous beads were observed with Environmental Scanning Electron Microscopy (FIG. 2, right)

Figure 3:
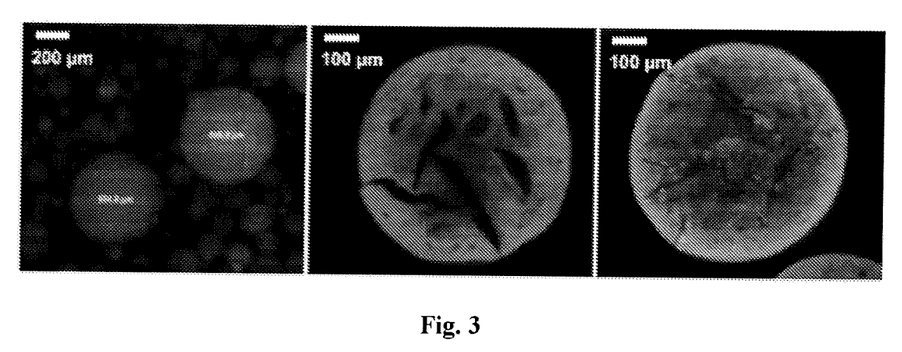
FIG. 3: Fluorescent porous beads prepared with FITC-dextran were observed with a fluorescent microscope before size calibration (left, size ranging from 20 µm to 1 mm) and after calibration (middle, diameter: 620 µm). Cell infiltration inside porous beads was assessed using confocal microscopy (right). Cells were identified by labeling with TRITC-phalloidin. Cells infiltrated the beads and were observed within the pores (mean diameter of beads: 660 µm)
Figure 4:
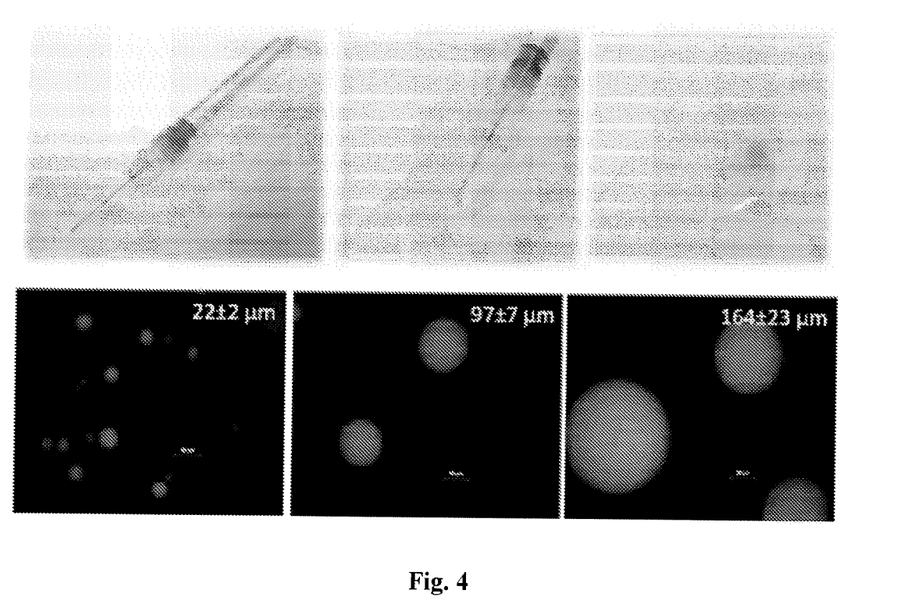
FIG. 4: Macroscopic views and confocal images of injectable porous microbeads. On the top left panel, beads were labeled with alcian blue to evidence the beads coming out of the needle. Different beads were prepared that varied in their size: 22±2 µm, 97±7 µm and 164±23 µm.

Interestingly, using a process of crosslinkinging, porous micro or macrobeads were obtained (FIG. 3, left). By changing the experimental conditions, micro/macro beads of different sizes could be obtained from 1 µm to a size higher than 1 mm. Polytron equipment provided beads with a size comprised between 1 and 30 µm, while using mechanical stirring provides beads with a size comprised between 10 µm and 1 mm (FIG. 4).

Through calibration, the inventors have met the burden to obtain a large scope of beads with different size. More precisely, the inventors have obtained polysaccharides heads according to the invention of a size of:

100 to 200 µm;
200 to 300 µm;

300 to 500 µm;
500 to 700 µm; and
700 to 1000 µm.

Cell Infiltration

The Inventors assessed cell infiltration inside porous microbeads using confocoal microscopy. After incubation of beads with human endothelial cells, the cell infiltration inside the FITC-labeled porous beads was thus observed (FIG. 3, middle and right panels).

Injection of the Beads

Figure 5:
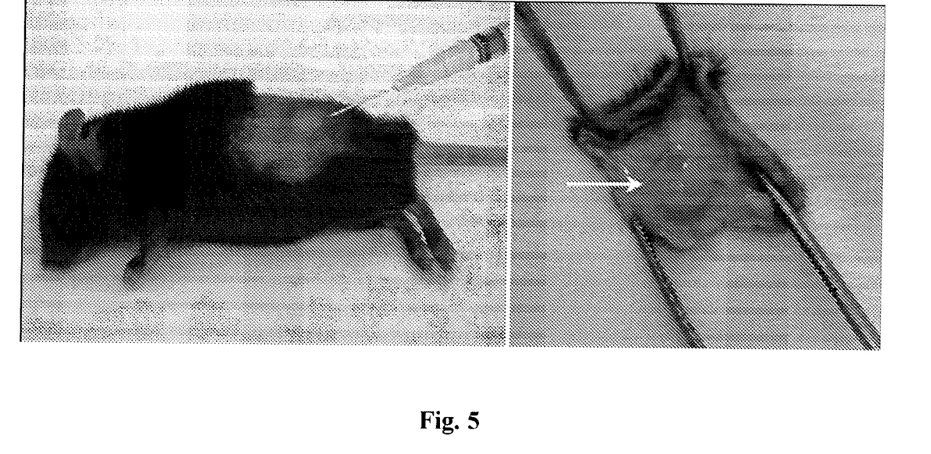
FIG. 5: Fluorescent beads were injected subcutaneously without leakage into a female C57 black mouse using a G25 gauge needle (left). Subcutaneous tissue was excised 24 hours later for histopathology analysis (right). Beads remained at the site of implantation and were visually assessed in the subcutaneous sample.

The microbeads of the invention have a size highly appropriate for injection through a needle (FIG. 4), and allow a depot of a bead suspension. Fluorescent beads (100-200 µm) were injected subcutaneously into female C57 black mice using a G25 gauge needle, with no immediate nor late leakage observed (FIG. 5). No reaction was observed at the injection site 24 hours later. After sacrifice, subcutaneous tissue was excised and analyzed with histopathology techniques.

Figure 6:
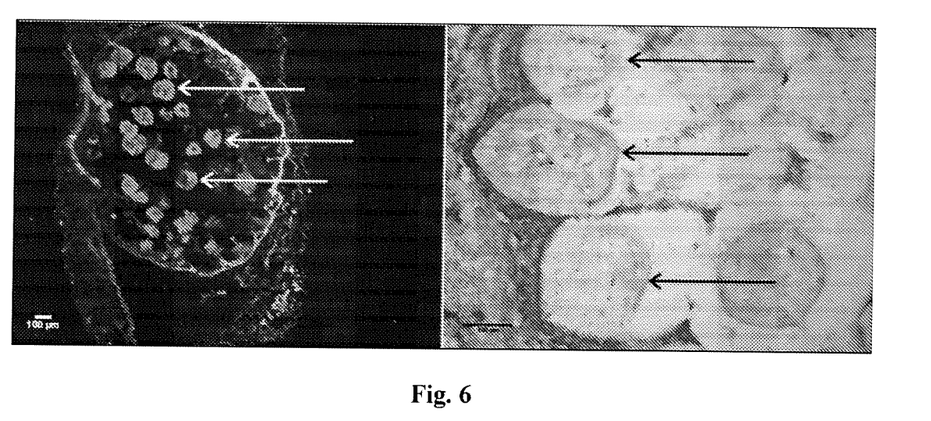
FIG. 6: Fluorescent beads (arrows) were observed on 8 µm sections of subcutaneous tissue 24 hours after injection (left, fluorescent microscopy). Beads (arrows) were also observed on alcian blue/nuclear red stained sections (right, light microscopy). Scale bars: 100 µm.

Beads were observed on 8 µm sections, either using a fluorescence microscope (FITC-labeled green beads and red autofluorescence background) or a light microscope following alcian blue/nuclear red staining protocols (FIG. 6).

Incorporation of Nano-Hydroxyapatite

Nano-hydroxyapatite (n-HA) was prepared by wet chemical precipitation using a 0.6M solution of Phosphoric acid (H3PO4 Rectapur, Prolabo®, France) and a 1M solution of calcium hydroxide (CaOH2 Alfa Aesar, Germany). The suspension of n-HA was included in the alkaline solution of polysaccharides in the starting solution at a 6% w/w. The resulting polysaccharide macrobeads contained n-HA dispersed in the 3D structure of the beads. The inventors have then discovered bone formation after implantation of the said beads in a condyle defect in rats.

Preparation of Polysaccharide Beads According to the Invention with a Thrombolytic Agent:

Beads according to the invention were prepared in the range of 1 to 10 microns containing tPA (American Diagnostica, tPA single-chain recombinant tissue plasminogen activator (tPA)).

9 g of pullulan, dextran 3 g, 1.2 g of fucoidan and 14 g NaCl in were mixed in 40 ml of water. 300 mg of the solution were isolated and 30 µL, of 10 M NaOH were added before mixing. 30 µL, of STMP (300 mg dissolved in 1 mL of STMP water) were then added. The mixture is injected into the oil (30 ml of canola oil, 0.35 mg of Span 80+Tween 80 0.12 mg) and the mixture was stirred with polytron (small propeller) at full speed for 2 minutes. The breaker is then put in an oven at 50° C. for 20 minutes. After removing the beaker from the oven, the mixture is balanced in 10× PBS under magnetic stirring for 30 min. The supernatant was removed and two rinses in 0.01% SDS, 3 rinses (1 h) in saline 0.025% NaCl were performed. Finally, a lyophilisation step is performed.

The inventors obtained different types of beads with the following composition of polysaccharide:
75% pullulan+25% dextran
25% DEAE pullulan, 75% neutral pullulan
50% pullulan+(25% dextran, 25% neutral dextran)
25% DEAE pullulan, 75% neutral pullulan,
50% DEAE dextran, 50% neutral dextran.

The activity was then assessed with 5 mg of beads in Eppendorf tubes. For this purpose, 50 µL of t-PA (200 UI/mL) or beads according to the invention containing t-Pa were incubated 1 hour, and rinsed 3 times with 500 L of buffer solution (PBS-0.1% HSA-0.01% Tween 20).

Colorimetric measurement after adding 50 µL of 2 mM substrate in S444 demonstrated that more than 30% of native t-PA activity was maintained in the beads.

Infiltration of Cells on Polysaccharide Heads According to the Invention

The seeding of the cells is performed in sterile 1.5 ml eppendorf tubes. In each of those tubes, 4 mg of lyophilized beads are placed within each tube. A cell suspension is prepared, containing from 2 to $3 \times 10^6$ cells in 15 to 20 µL of a culture medium for each of the eppendorf tubes. The cell suspension is placed within each eppendorf tube, which are then incubated for 30 min. 500 µL, of culture medium is then added in each tubes. The tubes are then incubated for 2 h at 37° C. in order to optimize the adhesion of the cells on the beads. The beads are then transferred in culture wells. 500 µL of culture medium is added to each wells. The cells are thus infiltrated in the beads of the invention and cultivated the appropriate time.

Figure 7:
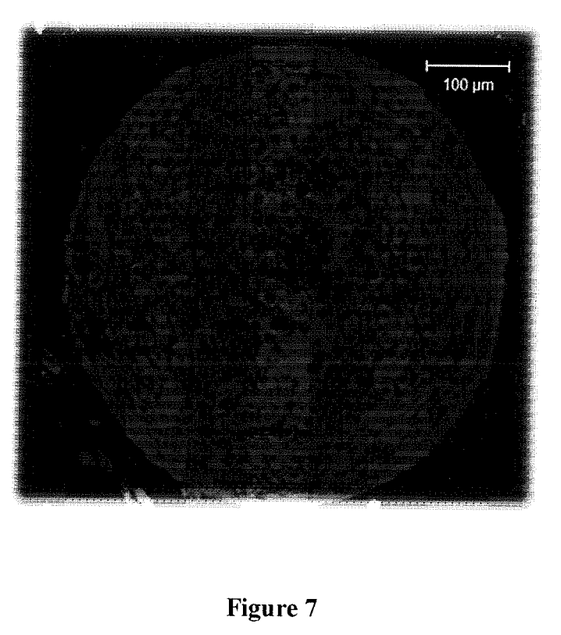
FIG. 7: Polysaccharide bead according to the invention covered with Fibroblast 3T3 after 2 days of culture.

The inventors performed said techniques for having heads infiltrated with: fibroblasts 3T3 (see FIG. 7), human umbilical vein endothelial cells, human mesenchymal stem cells, or lewis rat mesenchymal stem cells.

The inventors thus obtained polysaccharide bead comprising cultivated cells.

The invention claimed is:

1. A crosslinked polysaccharide bead having a spherical or ovoid shape obtained by
    a) preparing an alkaline aqueous solution comprising at least two polysaccharides and a cross linking agent;
    b) in the absence of surfactant, dispersing said alkaline aqueous solution into an hydrophobic phase consisting of a vegetal oil, in order to obtain a water-in-oil (w/o) emulsion; and
    c) transforming the w/o emulsion into beads by placing said w/o emulsion at a temperature from about 4° C. to about 80° C. for a sufficient time to allow the crosslinking of said at least two polysaccharides;
wherein said polysaccharides are selected from mixtures of dextran and pullulan, or mixtures of dextran, pullulan and fucoidan,
wherein said crosslinked polysaccharide bead is free of any organic solvent and surfactant, and
wherein said crosslinked polysaccharide bead has a mean diameter of more than 10 µm.

2. The bead according to claim 1, wherein the vegetal oil is selected from canola oil, corn oil, cottonseed oil, safflower oil, soybean oil, extra virgin olive oil, sunflower oil, palm oil, MCT oil, and trioleic oil.

3. The bead according to claim 2, wherein the vegetal oil is canola oil.

4. The bead according to claim 1, wherein the polysaccharide is a mixture of pullulan/dextran.

5. The bead according to claim 4, wherein the mixture of pullulan/dextran is in a ratio of 75:25 w/w.

6. The bead according to claim 1, wherein the cross-linking agent is selected from the group consisting of trisodium trimetaphosphate (STMP), phosphorus oxychloride ($POCl_3$), epichlorohydrin, formaldehydes, carbodiimides, and glutaraldehydes.

7. The bead according to claim 1, wherein the alkaline aqueous solution further comprises a porogen agent.

8. The bead according to claim 7, wherein the porogen agent is selected from the group consisting of sodium chloride, calcium chloride, ammonium carbonate, ammonium bicarbonate, calcium carbonate, sodium carbonate, sodium bicarbonate and mixtures thereof.

9. The bead according to claim 1, wherein the alkaline aqueous solution further comprises hydroxyapatite.

10. The bead according to claim 1, wherein the alkaline aqueous solution further comprises a drug.

* * * * *